(12) United States Patent
Frederiksen et al.

(10) Patent No.: US 11,460,457 B2
(45) Date of Patent: Oct. 4, 2022

(54) METHOD AND GAS FUSE FOR DETECTING A CORROSIVE GAS

(71) Applicant: Vitesco Technologies GmbH, Hannover (DE)

(72) Inventors: Finn Frederiksen, Schwalbach (DE); Heiko Jausel, Schwalbach (DE)

(73) Assignee: VITESCO TECHNOLOGIES GMBH, Hannover (DE)

( * ) Notice: Subject to any disclaimer, the term of this patent is extended or adjusted under 35 U.S.C. 154(b) by 0 days.

(21) Appl. No.: 17/254,976

(22) PCT Filed: Jun. 27, 2019

(86) PCT No.: PCT/EP2019/067241
§ 371 (c)(1),
(2) Date: Dec. 22, 2020

(87) PCT Pub. No.: WO2020/002547
PCT Pub. Date: Jan. 2, 2020

(65) Prior Publication Data
US 2021/0262999 A1    Aug. 26, 2021

(30) Foreign Application Priority Data
Jun. 27, 2018   (EP) .................................... 18180159

(51) Int. Cl.
G01N 33/00   (2006.01)
B01D 53/94   (2006.01)
F01N 13/00   (2010.01)

(52) U.S. Cl.
CPC ..... *G01N 33/0063* (2013.01); *B01D 53/9431* (2013.01); *F01N 13/008* (2013.01); *F01N 2560/02* (2013.01)

(58) Field of Classification Search
CPC combination set(s) only.
See application file for complete search history.

(56) References Cited

U.S. PATENT DOCUMENTS 2,878,354 A * 3/1959 Ellison .................... C23F 13/04
324/700
4,147,907 A    4/1979 Miindel
5,466,605 A   11/1995 Glaunsinger et al.
(Continued)

FOREIGN PATENT DOCUMENTS

CN    2260241 Y    8/1997
CN    206388304 U   8/2017
(Continued)

OTHER PUBLICATIONS

Office Action dated Nov. 29, 2021 issued in Chinese Patent Application No. 201980043235.X.
(Continued)

*Primary Examiner* — Binh Q Tran
(74) *Attorney, Agent, or Firm* — Cozen O'Connor

(57) ABSTRACT

A method for monitoring a concentration of a corrosive gas including at least observing at least one gas fuse, the gas fuse having at least one metal wire, which is configured for breaking due to corrosion if exposed to the corrosive gas in a way that a time-integrated concentration of the corrosive gas exceeds a critical value.

13 Claims, 1 Drawing Sheet

(56) References Cited

U.S. PATENT DOCUMENTS

| | | | |
|---|---|---|---|
| 7,388,386 B2* | 6/2008 | Ramgopal | G01N 17/04 |
| | | | 422/53 |
| 10,048,097 B2* | 8/2018 | Seimori | G01D 11/245 |
| 10,483,179 B2* | 11/2019 | Yasuda | H01L 23/49562 |
| 10,712,256 B2* | 7/2020 | Minamitani | G01N 27/20 |
| 2003/0068264 A1 | 4/2003 | Schmidt et al. | |
| 2006/0096862 A1* | 5/2006 | Benton | G01N 27/283 |
| | | | 204/431 |
| 2011/0011152 A1* | 1/2011 | Ito | G01N 27/4077 |
| | | | 73/23.31 |
| 2016/0153814 A1 | 6/2016 | Seimori et al. | |
| 2017/0089877 A1* | 3/2017 | Manley | G01N 33/1846 |

FOREIGN PATENT DOCUMENTS

| | | |
|---|---|---|
| EP | 2204555 | 7/2010 |
| GB | 201407575 | 4/2014 |
| JP | S 55-49127 | 4/1980 |
| JP | 2011-153056 | 8/2011 |
| KR | 20030074569 | 9/2003 |
| TW | 561916 U | 11/2003 |
| WO | WO 2015/166246 | 11/2015 |

OTHER PUBLICATIONS

Office Action dated Jul. 13, 2022 issued in Chinese Patent Application No. 201980043235.X.

\* cited by examiner

METHOD AND GAS FUSE FOR DETECTING A CORROSIVE GAS

CROSS REFERENCE TO RELATED APPLICATIONS

This is a U.S. national stage of Application No. PCT/EP2019/067241 filed Jun. 27, 2019. Priority is claimed on European Application No. EP 18180159.8 filed Jun. 27, 2018 the content of which is incorporated herein by reference.

BACKGROUND OF THE INVENTION

1. Field of the Invention

The invention relates to a method and a gas fuse for detecting a corrosive gas and for preventing damage caused by the corrosive gas.

2. Description of Related Art

In various contexts gases, in particular corrosive gases such as ammonia ($NH_3$) are handled within tanks or similar containers. Many such gases require safety measures, in particular relating to avoiding and/or detecting leakages within the containers they are kept within as well as to avoiding and/or detecting, if an excessive amount of such a gas diffuses through walls of such containers. This is particularly true for corrosive gases that might cause damages to, e.g., electronic components comprising copper wires or similar electronic connection lines. In particular, moist air comprising corrosive gases can be highly harmful to metals such as copper.

In the prior art there is no simple and cost efficient way to detect corrosive gases. Hence, minor leakages and/or excessive diffusion of the corrosive gas are likely to remain undetected. In particular, a permanent monitoring of corrosive gas concentrations is not possible with a simple cost efficient device.

SUMMARY OF THE INVENTION

It is, therefore, an object of one aspect of the present invention to overcome at least in part the disadvantages known from prior art and in particular to provide a gas fuse and a method for permanently monitoring a concentration of a corrosive gas in a simple and cost efficient way.

The method for monitoring a concentration of a corrosive gas according to one aspect of the present invention comprises at least observing at least one gas fuse. The gas fuse comprises at least one metal wire, which is configured for breaking due to corrosion if exposed to the corrosive gas in a way that a time-integrated concentration of the corrosive gas exceeds a critical value.

The corrosive gas can be any gas capable of corroding a metal. For example, the corrosive gas can be a mixture of an arbitrary gas and components such as ammonia, bromine, chloride, carbon dioxide, or others. Further, the corrosive gas may be a mixture of a multitude of different corrosive components.

The at least one metal wire can be made of any metal or of a mixture of materials comprising at least one metal that is sensitive to the corrosive gas. Therein, sensitive means that the metal wire can be corroded by the corrosive gas. For example, the metal wire can be made of copper and/or iron.

Preferably, the metal wire is electrically conductive. That is, an electric current preferably can be driven through the metal wire.

The time integrated concentration of the corrosive gas is supposed to be the value of the concentration of the corrosive gas the metal wire is exposed to, integrated over time. That means that a high concentration being present for a short period of time can have the same time integrated concentration value as a lower concentration being present over a longer period of time. The time integrated concentration is the relevant value in this context because it can be assumed that the corrosion takes place at a rate that is proportional or similarly related to the concentration of the corrosive gas. That is, a high concentration of the corrosive gas corrodes the metal wire faster than a lower concentration. That is, the time it takes until the metal wire breaks, depends on the corrosive gas concentration in the course of time. The time integrated concentration of the corrosive gas that is necessary to bring the metal wire to a breakage is the critical value.

With the gas fuse comprising the metal wire a long-time monitoring of the corrosive gas can be possible. That is, the long-term effect of corrosion is exploited here in contrast to, for example, the short-term effect of thermally breaking, which is used in electric fuses (used in other contexts). The long-term effect allows monitoring a concentration of the corrosive gas permanently over a long period of time in a simple and cost efficient way. Maintenance of the fuse is less frequently required and therefore further reducing costs.

The critical value of the time integrated concentration can be adapted to requirements of the certain application. The time it takes until the metal wire breaks depends particularly on the metal wire material and its cross section area. Both parameters in combination are restricted by the fact that a sufficiently strong current is supposed to flow through the metal wire in order to be able to detect whether or not the metal wire has been broken yet. Once the metal wire has broken, this can be detected electronically, indicating that the time integrated concentration of the corrosive gas has been exceeded.

In a preferred embodiment the method further comprises turning off at least one electronic component once the at least one metal wire has broken.

Damage to the at least one electronic component can be prevented by turning it off, for example because fault currents may be avoided.

In a further preferred embodiment the method further comprises sealing a leak once the at least one metal wire has broken.

Alternatively and/or additionally to the aforementioned turning-off of the at least one electronic component not only damage to electronic components is preferably prevented, but also defects such as leaks are preferably remedied.

In a further preferred embodiment of the method the corrosive gas comprises at least ammonia ($NH_3$).

The gas fuse being sensitive particularly for the corrosive gas comprising at least ammonia ($NH_3$) is advantageous because in various technologically important applications ammonia is present. Providing a gas fuse for detecting ammonia leakages and/or excessive diffusion of ammonia is particularly advantageous as ammonia can be harmful to health.

In a further preferred embodiment of the method the corrosive gas comprises at least water ($H_2O$).

In this context, water refers to the chemical substance represented by the formula $H_2O$, which can be present in any aggregate state, not necessarily in the liquid state. Water being comprised within the corrosive gas can facilitate the corrosion. In general, corrosion can be enhanced if a medium containing water surrounds the corrosive metal.

According to a further aspect of the present invention a gas fuse is provided for detecting a corrosive gas by the described method.

The details and advantages disclosed for the method are applicable to the gas fuse of the invention, and vice versa.

In a preferred embodiment of the gas fuse the at least one metal wire is made at least partially with copper.

Copper has, on the one hand, a good electric conductivity compared with other materials. On the other hand, copper has a reasonably high corrosivity, which makes it suitable for being used in the described gas fuse. That is, copper is a preferred material as it is a good compromise between the two requirements, the electric conductivity and the corrosivity.

In a further preferred embodiment of the gas fuse the at least one metal wire is held under tensile stress.

Therein, tensile stress means in particular that forces oriented away from each other act upon the two ends of the metal wire. Such a tensile stress can be provided, for example, by mounting the metal wire tightly into clamps or similar mounting devices. Further, springs or similar mechanical elements for creating forces can be integrated into the mounting installation for the metal wire. With the metal wire being held under tensile stress, not only the metal wire can break once the metal at one point of the metal wire has vanished completely due to corrosion, but also minor corrosion effects can be sufficient for the metal wire to no longer be able to withstand the tensile stress.

The at least one metal wire of the gas fuse is preferably electrically connected to a micro controller. The micro controller is preferably configured for processing information about the state of the metal wire. That is, once the metal wire has broken, the micro controller is supposed to output a corresponding signal. The corresponding output signal can be further used, for example, for preventing damage and/or for initiating a repair of defects. The output signal is preferably processed in a control device of a car.

The invention is preferably used in a selective catalyst reduction (SCR) dosing unit comprising at least one of the described gas fuses.

Selective catalyst reduction (SCR) is commonly used in automobiles for reducing pollutant substances in the exhaust gas. In particular, SCR units are used to reduce nitrogen oxides (NO, $NO_2$). Therefore, urea is introduced into the exhaust gas system. Thereby, particularly ammonia is included in the process. Preventing damage to electronic components also comprised within the SCR unit, or alternatively and/or additionally in the proximity of the SCR dosing unit, can be achieved with the described gas fuse. The gas fuse preferably fails before any substantial damage is done to the electronic components.

The metal wire may not only be sensitive to the corrosive gas, but also (indirectly) to a corrosive liquid. For example, the corrosive substance may be in its liquid state when penetrating through a leak and subsequently evaporate so that it affects the metal wire in its gaseous state. Alternatively, the corrosive liquid may directly affect the metal wire. This, however would be the case if there is a significant leak, which, usually, but not necessarily, is preceded by a minor leak, through which only a gas may diffuse. Thus, the metal wire can be affected by the minor leak prior to being exposed to the corrosive liquid.

The SCR dosing unit preferably comprises a urea handling space for containing urea, which in its gaseous state is a corrosive gas. Leakages of the urea handling space and/or excessive diffusion of the corrosive gas out of the urea handling space can be detected by the gas fuse in a simple and cost efficient way.

In particular, it is preferred that an electronic component is separated from the urea handling space by a plastic separating wall, which is in contact to (particularly liquid) urea on the side opposite to where the electronic component is situated. That is, the plastic separating wall preferably prevents the electronic component from being exposed to urea directly. However, urea may penetrate through leaks within the plastic separating wall and/or diffuse through the plastic separating wall. In both cases, the electronic component could be damaged by corrosion, which may be detected at an early stage by the described gas fuse.

The above described micro controller that is preferably electrically connected to the metal wire is preferably comprised within a casing of the SCR dosing unit. Alternatively, it is preferred that the micro controller is comprised within an external control unit.

BRIEF DESCRIPTION OF THE DRAWINGS

It should be noted that the individual features specified in the claims may be combined with one another in any desired technological reasonable manner and form further embodiments of the invention. The specification, in particular in connection with the figures, explains the invention further and specifies particularly preferred embodiments of the invention. Particularly preferred variants of the invention and also the technological field will now be explained in more detail on the basis of the enclosed figures. It should be noted that the exemplary embodiments shown in the figures are not intended to restrict the invention. The figures are schematic and may not be to scale. The figures display:

DETAILED DESCRIPTION OF THE PRESENTLY PREFERRED EMBODIMENTS

Figure 1:
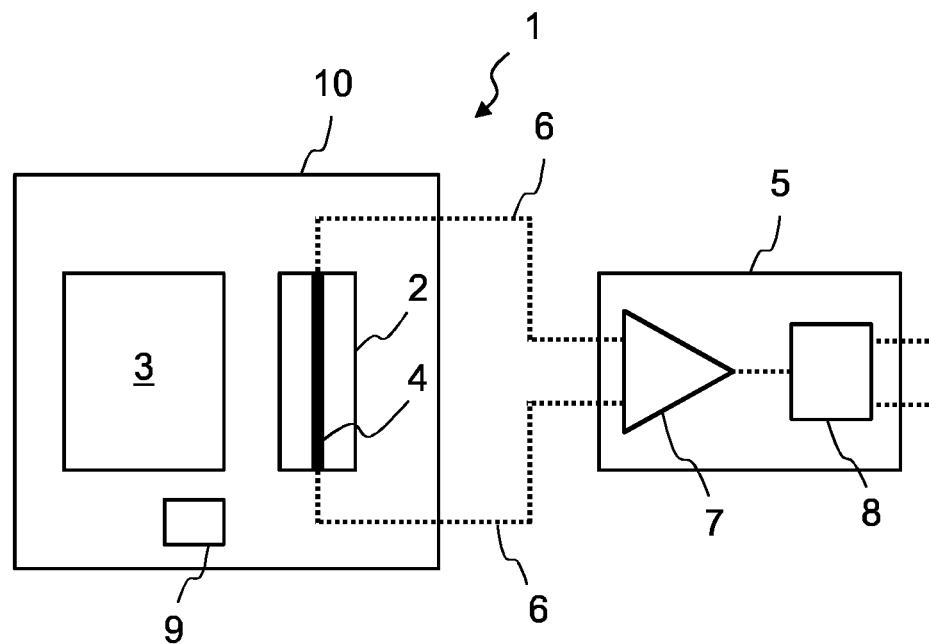
FIG. 1: is an SCR dosing unit comprising a gas fuse.

FIG. 1 shows an SCR dosing unit 1 comprising a gas fuse 2 having a metal wire 4. Further, the SCR dosing unit 1 comprises a urea handling space 3 and an electronic component 9, both of which being comprised within a casing 10. The metal wire 4 is connected to a micro controller 8 via cables 6, wherein an amplifier 7 is included in the connection for amplifying a current through the metal wire 4. Both the amplifier 7 and the micro controller 8 are comprised within a control unit 5.

Figure 2:
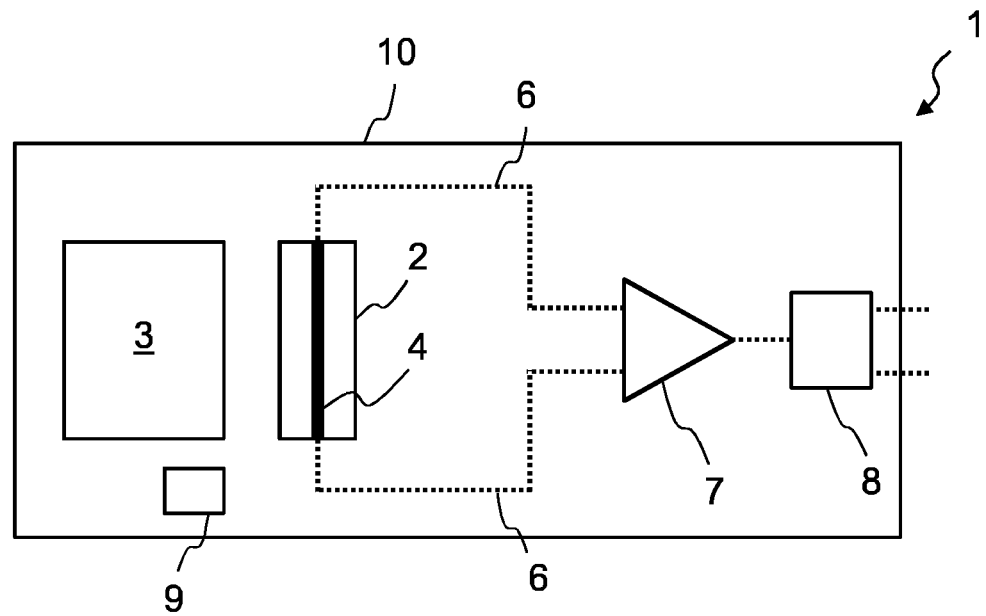
FIG. 2: is an SCR dosing unit comprising a gas fuse.

FIG. 2 displays a similar situation as shown in FIG. 1. Only here, the amplifier 7 and the micro controller 8 are not comprised within an external control unit, but within the casing instead.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A method for monitoring a concentration of a corrosive gas comprising:
 observing at least one gas fuse, the at least one gas fuse comprising at least one metal wire configured to break due to corrosion if exposed to the corrosive gas in a way that a time-integrated concentration of the corrosive gas exceeds a critical value,
 wherein the at least one metal wire is held under tensile stress such that respective ends of the at least one metal wire are subjected to forces oriented away from each other.

2. The method according to claim 1, further comprising turning off at least one electronic component once the at least one metal wire has broken.

3. The method according to claim 1, further comprising sealing a leak once the at least one metal wire has broken.

4. The method according to claim 1, wherein the corrosive gas comprises at least ammonia ($NH_3$).

5. The method according to claim 1, wherein the corrosive gas comprises at least water ($H_2O$).

6. A gas fuse configured to detect a corrosive gas comprising:
 a mount; and
 at least one metal wire having respective ends attached to the mount and configured to break due to corrosion if exposed to the corrosive gas in a way that a time-integrated concentration of the corrosive gas exceeds a critical value,
 wherein the respective ends of the at least one metal wire are biased away from each other by the mount.

7. The gas fuse according to claim 6, wherein the at least one metal wire is made at least partially with copper.

8. The gas fuse according to claim 6, wherein the at least one metal wire is held under tensile stress.

9. A selective catalyst reduction (SCR) dosing unit comprising:
 at least one gas fuse comprising:
  a mount; and
  at least one metal wire having respective ends attached to the mount and configured to break due to corrosion if exposed to the corrosive gas in a way that a time-integrated concentration of the corrosive gas exceeds a critical value,
  wherein the respective ends of the at least one metal wire are biased away from each other by the mount.

10. The method according to claim 1, wherein the respective ends of the at least one metal wire are biased away from each other by at least one spring element.

11. The method according to claim 1, further comprising outputting a signal indicating that the at least one metal wire is broken.

12. The gas fuse according to claim 6, wherein the mount comprises at least one spring element that biases the respective ends of the at least one metal wire away from each other.

13. The selective catalyst reduction (SCR) dosing unit according to claim 9, wherein the mount comprises at least one spring element that biases the respective ends of the at least one metal wire away from each other.

* * * * *